US011992559B2

(12) United States Patent
Spencer et al.

(10) Patent No.: US 11,992,559 B2
(45) Date of Patent: May 28, 2024

(54) MICROSPHERE FORMULATIONS COMPRISING LURASIDONE AND METHODS FOR MAKING AND USING THE SAME

(71) Applicant: Oakwood Laboratories, LLC, Oakwood Village, OH (US)

(72) Inventors: Colin Spencer, Cleveland, OH (US); Griffin Beyer, Cleveland, OH (US); Tracy Richey, Kent, OH (US); Mark Smith, Venetia, PA (US); Nicholas DeLucia, Mayfield Heights, OH (US)

(73) Assignee: Oakwood Laboratories, LLC, Oakwood Village, OH (US)

( * ) Notice: Subject to any disclaimer, the term of this patent is extended or adjusted under 35 U.S.C. 154(b) by 0 days.

(21) Appl. No.: 17/679,385

(22) Filed: Feb. 24, 2022

(65) Prior Publication Data

US 2022/0265562 A1 Aug. 25, 2022

Related U.S. Application Data

(60) Provisional application No. 63/267,403, filed on Feb. 1, 2022, provisional application No. 63/152,943, filed on Feb. 24, 2021.

(51) Int. Cl.
*A61K 9/50* (2006.01)
*A61K 31/496* (2006.01)
*A61K 47/34* (2017.01)

(52) U.S. Cl.
CPC .............. *A61K 9/50* (2013.01); *A61K 9/5089* (2013.01); *A61K 31/496* (2013.01); *A61K 47/34* (2013.01)

(58) Field of Classification Search
CPC ........ A61K 9/50; A61K 9/5089; A61K 47/34; A61K 31/496
See application file for complete search history.

(56) References Cited

U.S. PATENT DOCUMENTS

| | | | |
|---|---|---|---|
| 4,652,441 A | 3/1987 | Okada et al. | |
| 5,288,502 A | 2/1994 | McGinity et al. | |
| 8,158,152 B2 | 4/2012 | Palepu et al. | |
| 8,202,524 B2 | 6/2012 | Sah et al. | |
| 8,283,352 B2 | 10/2012 | Otoda et al. | |
| 8,343,513 B2 | 1/2013 | Thanoo et al. | |
| 8,728,528 B2 | 5/2014 | Biggs et al. | |
| 8,871,269 B2 | 10/2014 | Cook | |
| 8,900,636 B2 | 12/2014 | Cook | |
| 8,916,196 B2 | 12/2014 | Zeigerson | |
| 9,017,715 B2 | 4/2015 | Thanoo et al. | |
| 9,393,211 B2 | 7/2016 | Richey et al. | |
| 9,616,031 B2 | 4/2017 | Loo et al. | |
| 9,636,308 B2 | 5/2017 | Richey et al. | |
| 9,670,200 B2 | 6/2017 | Almarsson et al. | |
| 9,956,227 B2 | 5/2018 | Vanover et al. | |
| 9,999,670 B2 | 6/2018 | Perry et al. | |
| 2008/0069885 A1 | 3/2008 | Mesens et al. | |
| 2012/0077802 A1 | 3/2012 | Chytil et al. | |
| 2012/0091022 A1 | 4/2012 | Nakagawa et al. | |
| 2012/0202823 A1 | 8/2012 | Zeidan et al. | |
| 2015/0150791 A1* | 6/2015 | Gutierro Aduriz .. | A61K 31/519 514/259.41 |
| 2015/0157628 A1 | 6/2015 | Kannusamy et al. | |
| 2016/0024011 A1 | 1/2016 | Zeidan et al. | |
| 2016/0030351 A1 | 2/2016 | Richey et al. | |
| 2016/0220490 A1 | 8/2016 | Zeng et al. | |
| 2016/0310502 A1* | 10/2016 | Vanover .................. | A61P 43/00 |
| 2016/0317453 A1 | 11/2016 | Richey et al. | |
| 2017/0196802 A1 | 7/2017 | Ahmed et al. | |
| 2017/0196855 A1 | 7/2017 | Ahmed et al. | |
| 2019/0046532 A1 | 2/2019 | Konsoula et al. | |

FOREIGN PATENT DOCUMENTS

| | | | |
|---|---|---|---|
| EP | 724432 | 2/2018 | |
| WO | WO-2014202214 A1 * | 12/2014 | ........... A61K 31/519 |
| WO | 2014076712 | 3/2015 | |
| WO | 2018015915 | 1/2018 | |
| WO | WO-2018015915 A1 * | 1/2018 | |

OTHER PUBLICATIONS

Stahl, et al, Effectiveness of Lurasidone for Patients With Schizophrenia Following 6 Weeks of Acute Treatment With Lurasidone, Olanzapine, or Placebo: A 6-Month, Open-Label, Extension Study, 74 J Clin. Psych. 507 (Year: 2013).*
Pathak, et al, Preparation and Characterization of Intramuscular PLGA Based Microsphere, 9 J Drug Del. Therap. 127 (Year: 2019).*
Francesca Selmin, et al, Accelerated Polymer Biodegradation of Risperidone Poly(D,L-Lactide-Co-Glycolide) Microspheres, 13 AAPS Pharmscitech, 1465 (Year: 2012).*
Susan D'Souza, et al, Enhanced Degradation of Lactide-co-Glycolide Polymer with Basic Nucleophilic Drugs, Adv. Pharmaceutic. Article ID 154239 (Year: 2015).*

(Continued)

*Primary Examiner* — Sean M Basquill
(74) *Attorney, Agent, or Firm* — BENESCH, FRIEDLANDER, COPLAN & ARONOFF LLP

(57) ABSTRACT

Extended-release microsphere formulations comprising lurasidone are provided. In one aspect, the microsphere formulations are characterized in that the lurasidone is released in vivo in humans over a period of about 30 days. Methods for making and using the formulations are also provided.

16 Claims, 11 Drawing Sheets

(56) References Cited

OTHER PUBLICATIONS

Ece Ö BülBül, et al, Schizophrenia; A Review on Promising Drug Delivery Systems, 26 Curr. Pharm. Des. 3871 (Year: 2020).*

Khan S, Gangane PS, Mahapatra DK, Mahajan NM. Natural and Synthetic Polymers Assisted Development of Lurasidone Hydrochloride Intranasal Mucoadhesive Microspheres. Indian J of Pharmaceutical Education and Research. 2020;54(1):213-22.

Vay, K. et al; "Application of Hansen solubility parameters for understanding and prediction of drug distribution in microspheres"; Int. Journal of Pharmaceutics, vol. 416, Issue 1, 2011.

Newman, et al; Coamorphous Active Pharmaceutical Ingredient—Small Molecule Mixtures: Considerations in the Choice of Coformers for Enhancing Dissolution and Oral Bioavailability; Journal of Pharmaceutical Sciences, vol. 107, Issue 1, 2018.

Dhapte, V. et al; "Advances in hydrotropic solutions: An updated review"; St. Petersburg Polytechnical University Journal: Physics and Mathematics, vol. 1, Issue 4, 2015.

Riebesehl, Bernd; "Chapter 29—Drug Delivery with Organic Solvents or Colloidal Dispersed Systems"; Editor(s): Camille Georges Wermuth, David Aldous, Pierre Raboisson, Didier Rognan, The Practice of Medicinal Chemistry (Fourth Edition), Academic Press, 2015.

Kinoshita, M. et al; "Entropic enrichment of cosolvent near a very large solute immersed in solvent-cosolvent binary mixture: Anomalous dependence on bulk cosolvent concentration"; Journal of Molecular Liquids, vol. 247, 2017.

International Search Report and Written Opinion issued in PCT/US2022/070807, mailing date May 6, 2022.

* cited by examiner

▲ Batch No. 4
△ Batch No. 4I

MICROSPHERE FORMULATIONS COMPRISING LURASIDONE AND METHODS FOR MAKING AND USING THE SAME

CROSS-REFERENCE TO RELATED APPLICATIONS

This application claims priority from U.S. Provisional Patent Application No. 63/267,403, filed on Feb. 1, 2022, and U.S. Provisional Patent Application No. 63/152,943, filed on Feb. 24, 2021, each of which is incorporated by reference herein in its entirety.

BACKGROUND

Lurasidone (chemical formula $C_{28}H_{36}N_4O_2S$; CAS Number 367514-87-2), characterized by the general structure:

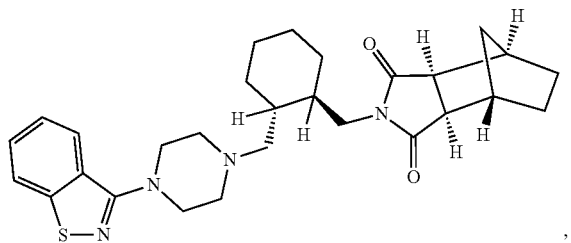 [SMILES: O=C1[C@@H]2[C@H]3CC[C@H](C3)[C@@H]2C(=O)N1C[C@@H]1CCCC[C@H]1CN1CCN(c2nsc3ccccc23)CC1]

is a known antipsychotic medication used to treat schizophrenia and depression in people with bipolar disorder. Lurasidone is currently orally administered with a tablet (commercially available under the trade name Latuda®). However, long term maintenance treatment through this route is problematic, as it creates withdrawal symptoms due to the steep rise and drop of the drug concentrations in plasma after each dose. Patient compliance and the potential for abuse are also drawbacks for this method of treatment.

An existing product for the treatment of schizophrenia, Risperdal® Consta®, is a two-week release microsphere formulation wherein risperidone is micro-encapsulated in Poly(D,L-lactide-co-glycolide), 75:25. However, some patients experience side effects from using Risperdal® Consta® and may require another treatment option.

Thus, a need exists for an extended release lurasidone-encapsulating microsphere formulation, especially a microsphere formulation that has a high drug load, a small particle size, and a low initial burst release.

SUMMARY

Microsphere formulations comprising lurasidone are provided. The microsphere formulations comprise polymer microspheres, each polymer microsphere comprising: (i) lurasidone; and (ii) a biodegradable polymer, wherein each polymer microsphere comprises a drug load of lurasidone of greater than 55% by weight of the polymer microsphere, and wherein the polymer microspheres have an average particle size of less than 25 μm ($D_{50}$). In one aspect, the microsphere formulations are characterized in that at least 50% of the lurasidone is released over a period of about 30 days (i.e., ±10% of 30 days or 27 days to 33 days) of injection into a subject. In another aspect, the microsphere formulations are characterized in that they have a low initial burst release, that is, not more than 20% of the lurasidone is released within about 24 hours of injection into a subject. In another aspect, the microsphere formulations are sterilized by irradiation.

In one aspect, the microsphere formulations may be made by a method, the method comprising: (A) mixing: (i) the biodegradable polymer; (ii) a primary solvent; (iii) lurasidone; and (iv) a co-solvent, to form a dispersed phase; (B) mixing: (i) water; (ii) a surfactant; and, optionally, (iii) a buffer, to form a continuous phase; and (C) combining the dispersed phase with the continuous phase in a homogenizer. In another aspect, the method further comprises sterilizing the microsphere formulations by irradiation.

In one aspect, a method for treating schizophrenia and/or depression in a subject suspected of having bipolar disorder is provided. The method may comprise administering by intra-articular, intramuscular, or subcutaneous injection to a patient in need thereof a microsphere formulation made according to the methods described herein, wherein the formulation is administered to the patient with a dosing schedule of about every 30 days.

In another aspect, use is disclosed of a microsphere formulation comprising polymer microspheres, each polymer microsphere comprising: (i) lurasidone; and (ii) a biodegradable polymer, wherein each polymer microsphere comprises a drug load of lurasidone of greater than 55% by weight of the polymer microsphere, and wherein the polymer microspheres have an average particle size of less than 25 μm ($D_{50}$), in the manufacture of a medicament for the treatment of schizophrenia and/or depression in a subject suspected of having bipolar disorder.

In another aspect, a microsphere formulation comprising polymer microspheres, each polymer microsphere comprising: (i) lurasidone; and (ii) a biodegradable polymer, wherein each polymer microsphere comprises a drug load of lurasidone of greater than 55% by weight of the polymer microsphere, and wherein the polymer microspheres have an average particle size of less than 25 μm ($D_{50}$), is provided for use as a medicament for the treatment of schizophrenia and/or depression in a subject suspected of having bipolar disorder.

In another aspect, a kit is provided, the kit comprising polymer microspheres, each polymer microsphere comprising: (i) lurasidone; and (ii) a biodegradable polymer, wherein each polymer microsphere comprises a drug load of lurasidone of greater than 55% by weight of the polymer microsphere, and wherein the polymer microspheres have an average particle size of less than 25 μm ($D_{50}$).

DETAILED DESCRIPTION

Figure 1:
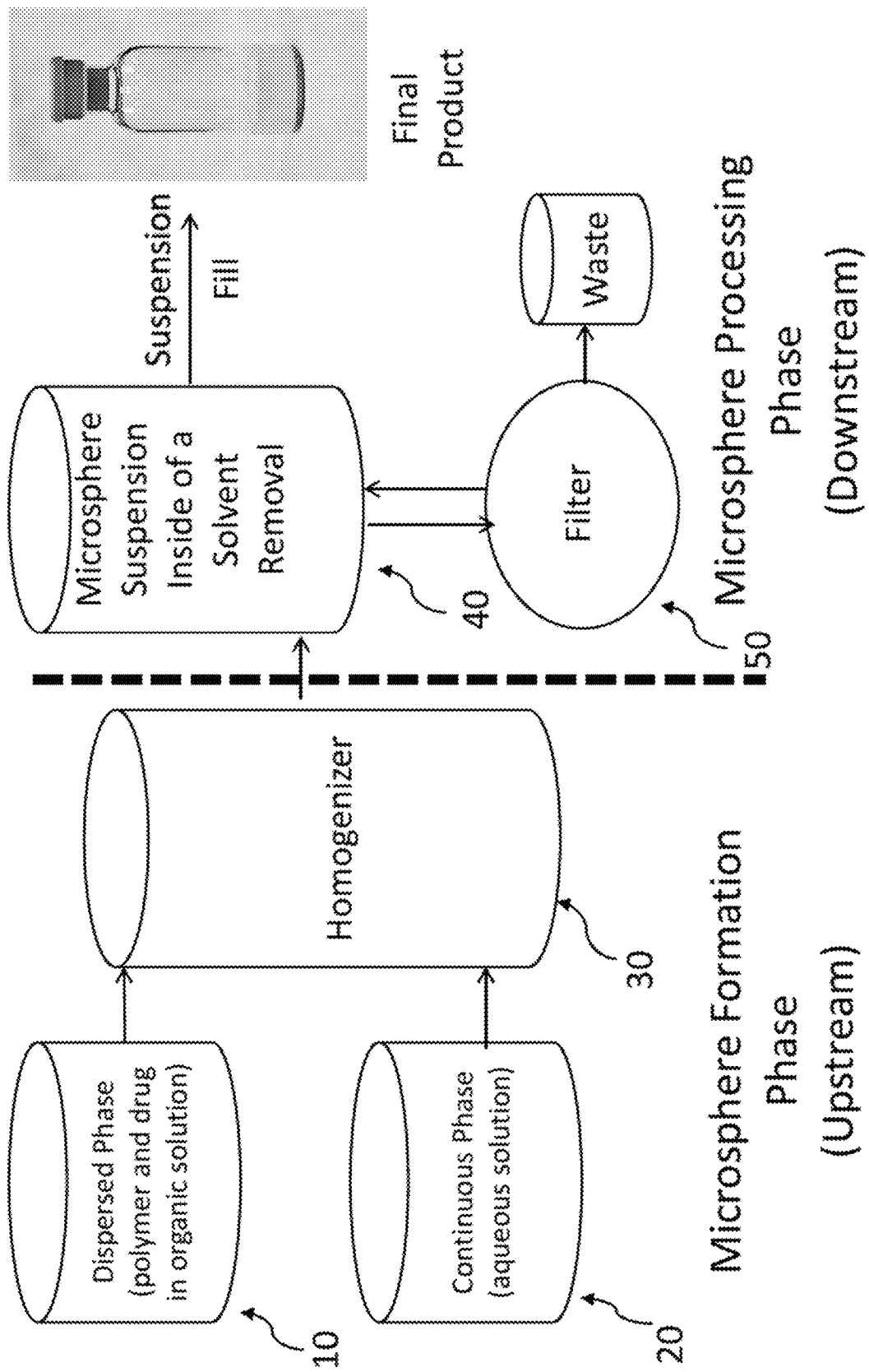
FIG. 1 is a schematic depicting a method for making lurasidone-encapsulated polymer microspheres.

Microsphere formulations comprising lurasidone are provided. In one aspect, the microsphere formulations comprise polymer microspheres, each polymer microsphere comprising: (i) lurasidone; and (ii) a biodegradable polymer, wherein each polymer microsphere comprises a drug load of lurasidone of greater than 55% by weight of the polymer microsphere, and wherein the polymer microspheres have an average particle size of less than 25 µm ($D_{50}$). In one aspect, the microsphere formulations are characterized in that the lurasidone is released over a period of about 30 days.

In one aspect, the microsphere formulations may be made by a method, the method comprising: (A) mixing: (i) the biodegradable polymer; (ii) a primary solvent; (iii) lurasidone; and (iv) a co-solvent, to form a dispersed phase; (B) mixing: (i) water; (ii) a surfactant; and, optionally, (iii) a buffer, to form a continuous phase; and (C) combining the dispersed phase with the continuous phase in a homogenizer.

Lurasidone

In one aspect, the lurasidone is lurasidone HCl supplied by Procos S.p.A., having a specific hydrophobicity of log $P_{ow}$=5.6 (at 25° C.), pKa=7.6, 8.5, water solubility of 0.224 mg/mL, solubility in dichloromethane of 24.43 mg/g, and solubility in benzyl alcohol of 69.19 mg/g.

Biodegradable Polymers

In one aspect, the dispersed phase may include a biodegradable polymer, such as poly (D,L-lactide-co-glycolide) ("PLGA"), a poly(L-lactide) ("PLA"), or a poly(D,L-lactide) ("PLDA"), although it is contemplated that other suitable biodegradable polymers may be used. The biodegradable polymer may be hydrophobic or hydrophilic. In one aspect, the biodegradable polymer is hydrophobic. In another aspect, the biodegradable polymer has an inherent viscosity of about 0.14 dL/g to about 0.56 dL/g, including from about 0.14 dL/g to about 0.29 dL/g, and including 0.19 dL/g, 0.20 dL/g, 0.21 dL/g, 0.29 dL/g, and 0.56 dL/g. In one aspect, the biodegradable polymer comprises Viatel™ DLG 7502A, Poly(D,L-lactide-co-glycolide), acid terminated, lactide:glycolide 75:25, manufactured by Ashland, having IV=0.19 ("7502A"). In one aspect, the biodegradable polymer comprises Viatel™ DLG 7503A, Poly(D,L-lactide-co-glycolide), acid terminated, lactide:glycolide 75:25, manufactured by Ashland, having IV=0.29 ("7503A"). In one aspect, the biodegradable polymer comprises Resomer® RG 752 H, Poly(D,L-lactide-co-glycolide), acid terminated, lactide:glycolide 75:25, manufactured by Evonik Rohm GmbH, having IV=0.21 dL/g ("752 H"). In one aspect, the biodegradable polymer comprises Viatel™ DLG 7507A, Poly(D,L-lactide-co-glycolide), acid terminated, lactide:glycolide 75:25, manufactured by Ashland, having IV=0.56 ("7507A").

Dispersed Phase

In one aspect, the dispersed phase comprises a primary solvent. In one aspect, the primary solvent comprises dichloromethane (DCM). The dispersed phase may also include up to about 50% by weight of a co-solvent capable of optimizing the solubility of lurasidone in the primary solvent. In one aspect, the co-solvent may be benzyl alcohol (BA), dimethyl sulfoxide, dimethyl formamide, dimethyl acetamide, acetonitrile, ethanol, N-methyl pyrrolidone, ethyl acetate, or any other solvent that increases the solubility of lurasidone in the dispersed phase containing DCM. In one aspect, the primary solvent comprises DCM, and the co-solvent comprises BA. In one aspect, the ratio of DCM to BA is about 2: about 1. The organic solvent is removed from the microspheres during their preparation. A microsphere is "essentially free" of organic solvent if the microsphere meets the standards set forth in the "ICH Harmonised Guideline, Impurities: Guideline for Residual Solvents Q3C(R8), Current Step 4 version dated 22 Apr. 2021," which is incorporated herein by reference in its entirety.

Continuous Phase

The dispersed phase may be combined with an aqueous continuous phase that comprises water and, optionally, a buffer, a surfactant, or both.

In one aspect, the buffer may be added to the continuous phase to maintain a pH of the solution of about 7.0 to about 8.0. In one aspect, the buffer may be a phosphate buffer or a carbonate buffer. In one aspect, the buffer may be a 10 mM phosphate or carbonate buffer solution and may be used to create and maintain a system pH level of about 7.6.

The surfactant component may be present in the continuous phase in an amount of about 0.35% to about 1.0% by weight in water. In one aspect, the surfactant component comprises polyvinyl alcohol ("PVA") in a concentration of 0.35% by weight in water.

In some aspects, the dispersed phase flow rate to the homogenizer may be from about 10 mL/min to about 30 mL/min, including about 20 mL/min and about 25 mL/min. In some aspects, the continuous phase flow rate to the homogenizer may be about 2 L/min. Thus, in one aspect, the continuous phase:dispersed phase ratio may be from about 66:1 to about 200:1, including about 100:1 and about 80:1.

The continuous phase may be provided at room temperature or above or below room temperature. In some aspects, the continuous phase may be provided at about 40° C., about 37° C., about 35° C., about 30° C., about 25° C., about 20° C., about 15° C., about 10° C., about 5° C., about 0° C., and any range or value between any of those values.

Homogenizer

For brevity, and because the methods are equally applicable to either, the phrase "homogenizer" contemplates a system or apparatus that can homogenize the dispersed phase and the continuous phase, emulsify the dispersed phase and the continuous phase, or both, which systems and apparatuses are known in the art. For example, in one aspect, the homogenizer is an in-line Silverson Homogenizer (commercially available from Silverson Machines, Waterside UK) or a Levitronix® BPS-i100 integrated pump system used, e.g., as described in U.S. Pat. No. 11,167,256, which is incorporated by reference herein in its entirety. In one aspect, the homogenizer is a membrane emulsifier. In one aspect, the homogenizer runs at an impeller speed of about 1,000 to about 4,000 revolutions per minute (RPM), including about 1,600 RPM, about 2,500 RPM, and about 3,500 RPM.

Drug Load

The drug load of each polymer microsphere in a drug to polymer ratio, expressed as a percentage, may range from greater than 55 wt/wt % to about 70 wt/wt %, from about 60 wt/wt % to about 70 wt/wt %, from about 60 wt/wt % to about 65 wt/wt %, from about 65 wt/wt % to about 70 wt/wt %, greater than 55 wt/wt %, and greater than 60 wt/wt %.

Particle Size

In one aspect, the polymer microspheres may have an average particle size between 10 μm ($D_{50}$) and 30 μm ($D_{50}$), less than about 20 μm ($D_{50}$), less than 25 μm ($D_{50}$), and between 14 μm ($D_{50}$) and 25 μm ($D_{50}$).

Extended Release

The microsphere formulations are characterized in that they have an in vivo duration of release of about 30 days in humans. In one aspect, the microsphere formulations are characterized in that at least about 50%, at least about 60%, at least about 70%, at least about 80%, at least about 90%, or 100%, and any range between any of those values, of the lurasidone is released over a period of about 30 days of injection into a subject. For example, in one aspect, the microsphere formulations are characterized in that about 75% to 100% of the lurasidone is released over a period of about 30 days of injection into a subject. In another aspect, the microsphere formulations are characterized in that they have a low initial burst release, that is, not more than about 20% of the lurasidone is released within about 24 hours of injection into a subject.

Therapeutic Benefits

Possible conditions that may be treated using the lurasidone microsphere formulations comprising lurasidone include schizophrenia and depression in people with bipolar disorder. In one aspect, schizophrenia and depression may be treated using the microsphere formulations comprising lurasidone, wherein the microsphere formulations are administered about every 30 days.

In one aspect, a method for treating schizophrenia and/or depression in a subject suspected of having bipolar disorder is provided. The method may comprise administering by intra-articular, intramuscular, or subcutaneous injection to a patient in need thereof a microsphere formulation made according to the methods described herein, wherein the formulation is administered to the patient with a dosing schedule of about every 30 days.

In another aspect, use is disclosed of a microsphere formulation comprising polymer microspheres, each polymer microsphere comprising: (i) lurasidone; and (ii) a biodegradable polymer, wherein each polymer microsphere comprises a drug load of lurasidone of greater than 55% by weight of the polymer microsphere, and wherein the polymer microspheres have an average particle size of less than 25 μm ($D_{50}$), in the manufacture of a medicament for the treatment of schizophrenia and/or depression in a subject suspected of having bipolar disorder.

In another aspect, a microsphere formulation comprising polymer microspheres, each polymer microsphere comprising: (i) lurasidone; and (ii) a biodegradable polymer, wherein each polymer microsphere comprises a drug load of lurasidone of greater than 55% by weight of the polymer microsphere, and wherein the polymer microspheres have an average particle size of less than 25 μm ($D_{50}$), is provided for use as a medicament for the treatment of schizophrenia and/or depression in a subject suspected of having bipolar disorder.

In another aspect, a kit is provided, the kit comprising polymer microspheres, each polymer microsphere comprising: (i) lurasidone; and (ii) a biodegradable polymer, wherein each polymer microsphere comprises a drug load of lurasidone of greater than 55% by weight of the polymer microsphere, and wherein the polymer microspheres have an average particle size of less than 25 μm ($D_{5o}$).

EXAMPLES

Example 1

General Preparation of Polymer Microspheres Comprising Lurasidone

Microsphere Formation Phase. With reference to FIG. 1, a dispersed phase ("DP") 10 is formed by dissolving a polymer matrix (such as a PLGA polymer) in an organic solvent system (such as DCM and BA), followed by the addition of lurasidone with mixing until completely dissolved. The DP 10 is filtered using a 0.2 μm sterilizing PTFE or PVDF membrane filter (such as EMFLON, commercially available from Pall or SartoriousAG) and pumped into a homogenizer 30, such as an in-line Silverson Homogenizer (commercially available from Silverson Machines, Waterside UK) or a Levitronix i100 (as described in U.S. Pat. No. 11,167,256), at a defined flow rate. A continuous phase ("CP") 20 comprising water, surfactant, and buffer is also pumped into the homogenizer 30 at a defined flow rate. The speed of the homogenizer 30 is generally fixed to achieve a desired polymer microsphere size distribution. A representative continuous "upstream" microsphere formation phase is described in U.S. Pat. No. 5,945,126, which is incorporated by reference herein in its entirety.

Microsphere Processing Phase. The formed or forming microspheres exit the homogenizer 30 and enter a solvent removal vessel ("SRV") 40. Water may be added to the SRV 40 during microsphere formation to minimize the solvent level in the aqueous medium. After the DP 10 has been exhausted, the CP 20 and water flow rates are stopped, and the washing steps are initiated. Solvent removal is achieved using water washing and a hollow fiber filter (commercially available as HFF from Cytiva) 50. A representative "downstream" microsphere processing phase is described in U.S. Pat. No. 6,270,802, which is incorporated by reference herein in its entirety.

The washed microspheres are collected and freeze-dried in a lyophilizer (Virtis) to remove any moisture. The resulting microspheres are a free-flowing off-white bulk powder.

Example 2

Preparation of Lurasidone-Encapsulated Polymer Microspheres—Batch No. 1

Following the general procedure described in Example 1 and illustrated in FIG. 1, the DP was formed by dissolving 400 g of 752 H polymer (IV=0.21 dL/g) in 4,000 g of DCM and 2,000 g of BA (DCM/BA (2:1)), followed by addition of lurasidone (600 g) with mixing until completely dissolved. The DP was filtered and pumped into a Levitronix® BPS-i100 integrated pump system operating at 3,000 RPM. The CP comprising 0.35% PVA and phosphate buffer (pH=7.6) was also pumped into the homogenizer at a defined flow rate.

The formed or forming microspheres exited the homogenizer and entered the SRV. Deionized water was added to the SRV. Solvent removal was achieved using water washing and a hollow fiber filter. The bulk suspension was collected via filtration and lyophilized to obtain a free-flowing powder. The resulting microspheres had an average particle size of 9.2 ($D_{50}$) and a drug load of 66.7%.

Example 3

Preparation of Lurasidone-Encapsulated Polymer Microspheres—Batch No. 2

Following the general procedure described in Example 1 and illustrated in FIG. 1, the DP was formed by dissolving 400 g of 752 H polymer (IV=0.21 dL/g) in 4,000 g of DCM and 2,000 g of BA (DCM/BA (2:1)), followed by addition of lurasidone (600 g) with mixing until completely dissolved. The DP was filtered and pumped into a Levitronix® BPS-i100 integrated pump system operating at 4,000 RPM. The CP comprising 0.35% PVA and phosphate buffer (pH=7.6) was also pumped into the homogenizer at a defined flow rate.

The formed or forming microspheres exited the homogenizer and entered the SRV. Deionized water was added to the SRV. Solvent removal was achieved using water washing and a hollow fiber filter. The bulk suspension was collected via filtration and lyophilized to obtain a free-flowing powder. The resulting microspheres had an average particle size of 14.8 ($D_{50}$) and a drug load of 65.5%.

Figure 2:
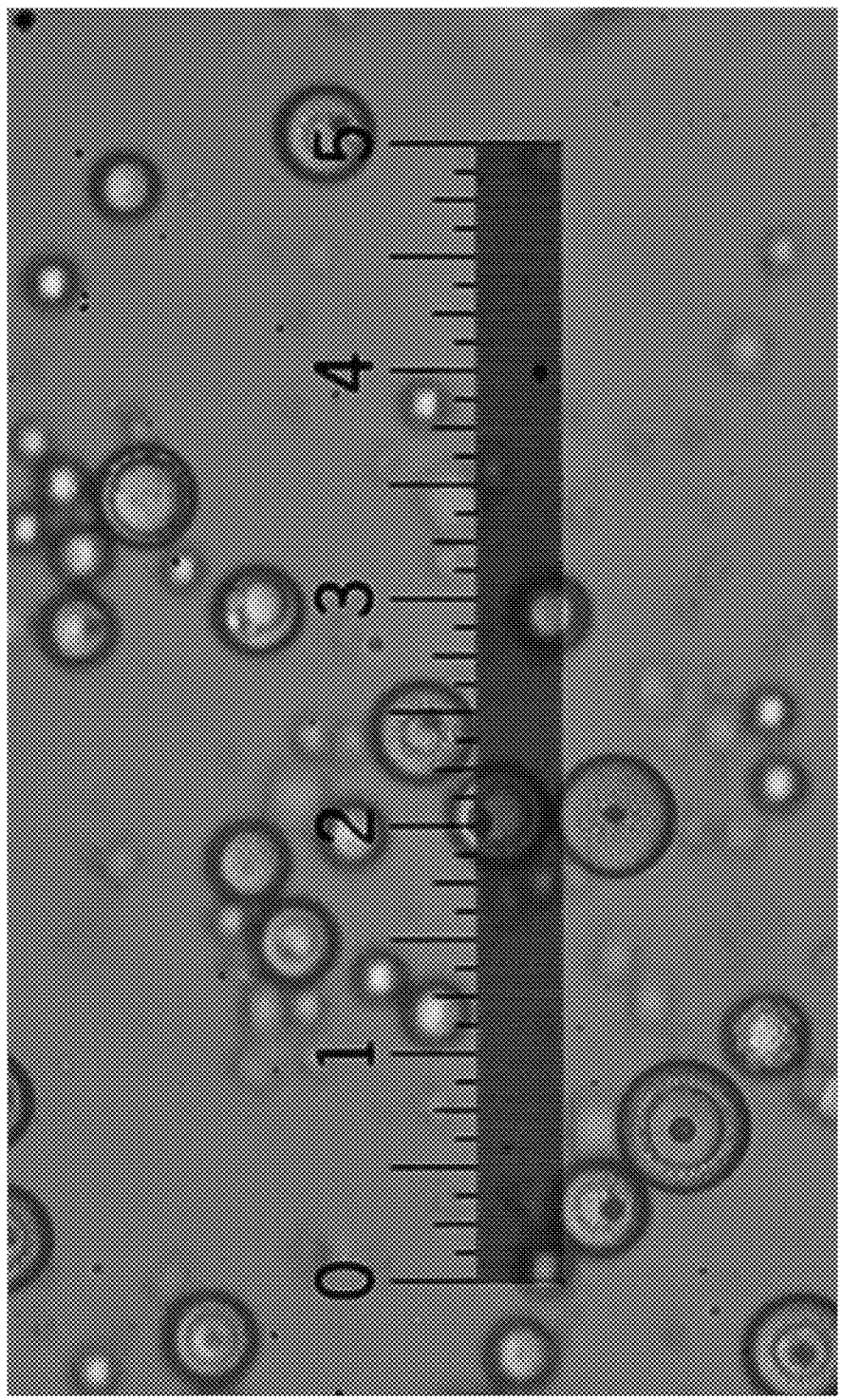
FIG. 2 is a microscope image of lurasidone-encapsulating polymer microspheres.

FIG. 2 is a microscope image of lurasidone-encapsulating polymer microspheres from Batch No. 2.

Figure 3:
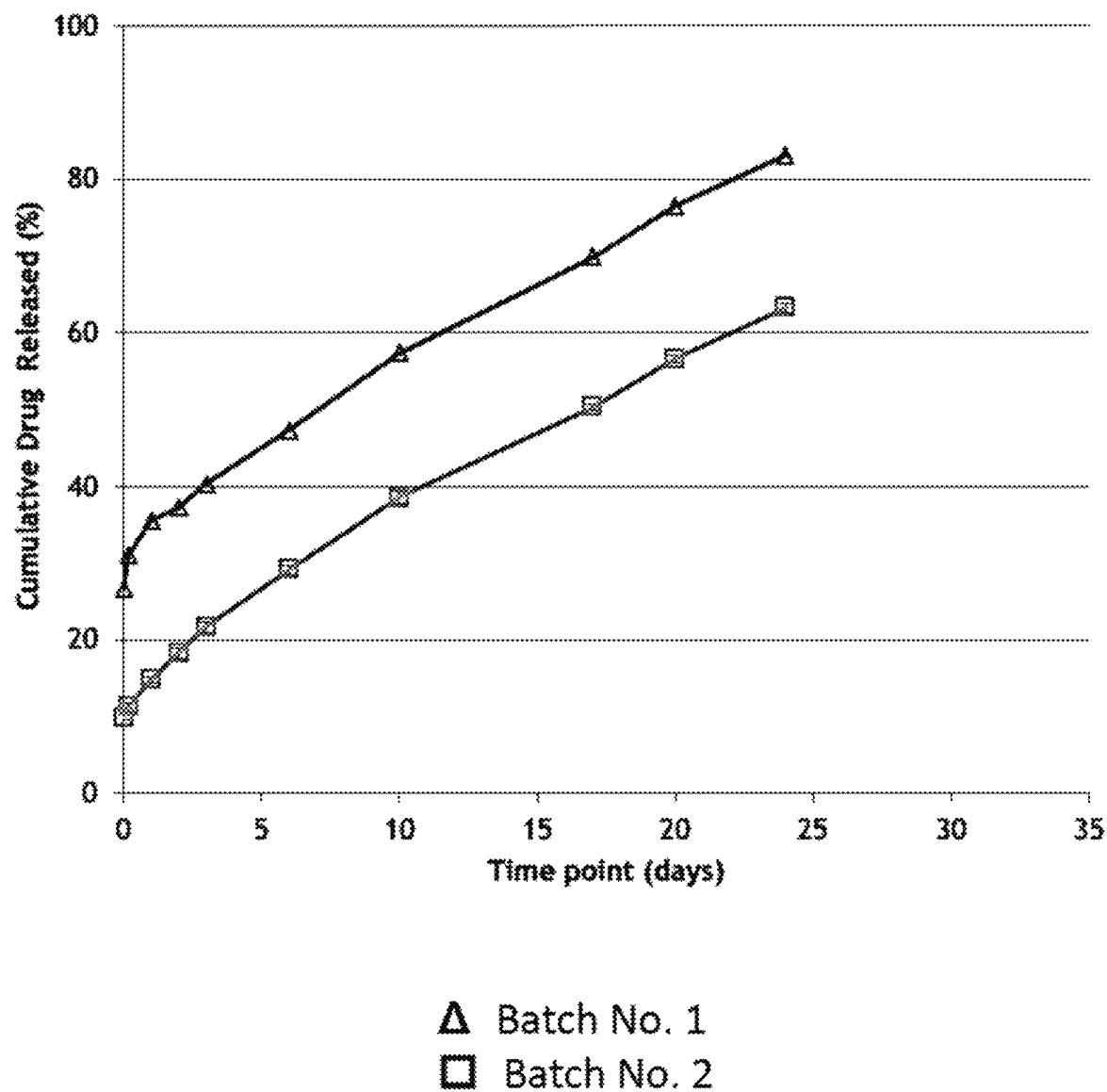
FIG. 3 is a graph showing in vitro cumulative lurasidone release over time from lurasidone-encapsulating polymer microspheres.

FIG. 3 is a graph comparing the cumulative lurasidone release over time from Batch No. 1 versus Batch No. 2.

Example 4

Preparation of Lurasidone-Encapsulated Polymer Microspheres—Batch Nos. 3 & 3I

Following the general procedure described in Example 1 and illustrated in FIG. 1, the DP was formed by dissolving 120 g of 7502A polymer (IV=0.20 dL/g) in 800 g of DCM and 400 g of BA (DCM/BA (2:1)), followed by addition of lurasidone (180 g) with mixing until completely dissolved. The DP was filtered and pumped at a flow rate of 25 mL/min into a Levitronix® BPS-i100 integrated pump system operating at 2,500 RPM. The CP comprising 0.35% PVA and 10 mM phosphate buffer (pH=7.6) was also pumped into the homogenizer at a flow rate of 2 L/min (CP:DP=80:1).

The formed or forming microspheres exited the homogenizer and entered the SRV. Deionized water was added to the SRV. Solvent removal was achieved using water washing and a hollow fiber filter. The bulk suspension was collected via filtration and lyophilized to obtain a free-flowing powder.

A portion of the powder was subjected to 25 kGy gamma irradiation under ambient temperature. The non-irradiated portion (Batch No. 3) had an average particle size of 22 μm ($D_{50}$), a drug load of 60.4 wt %, and a molecular weight of 16.9 kDa. The irradiated portion (Batch No. 3I) had an average particle size of 21 μm ($D_{50}$), a drug load of 60.2 wt %, and a molecular weight of 15.8 kDa.

Figure 4:
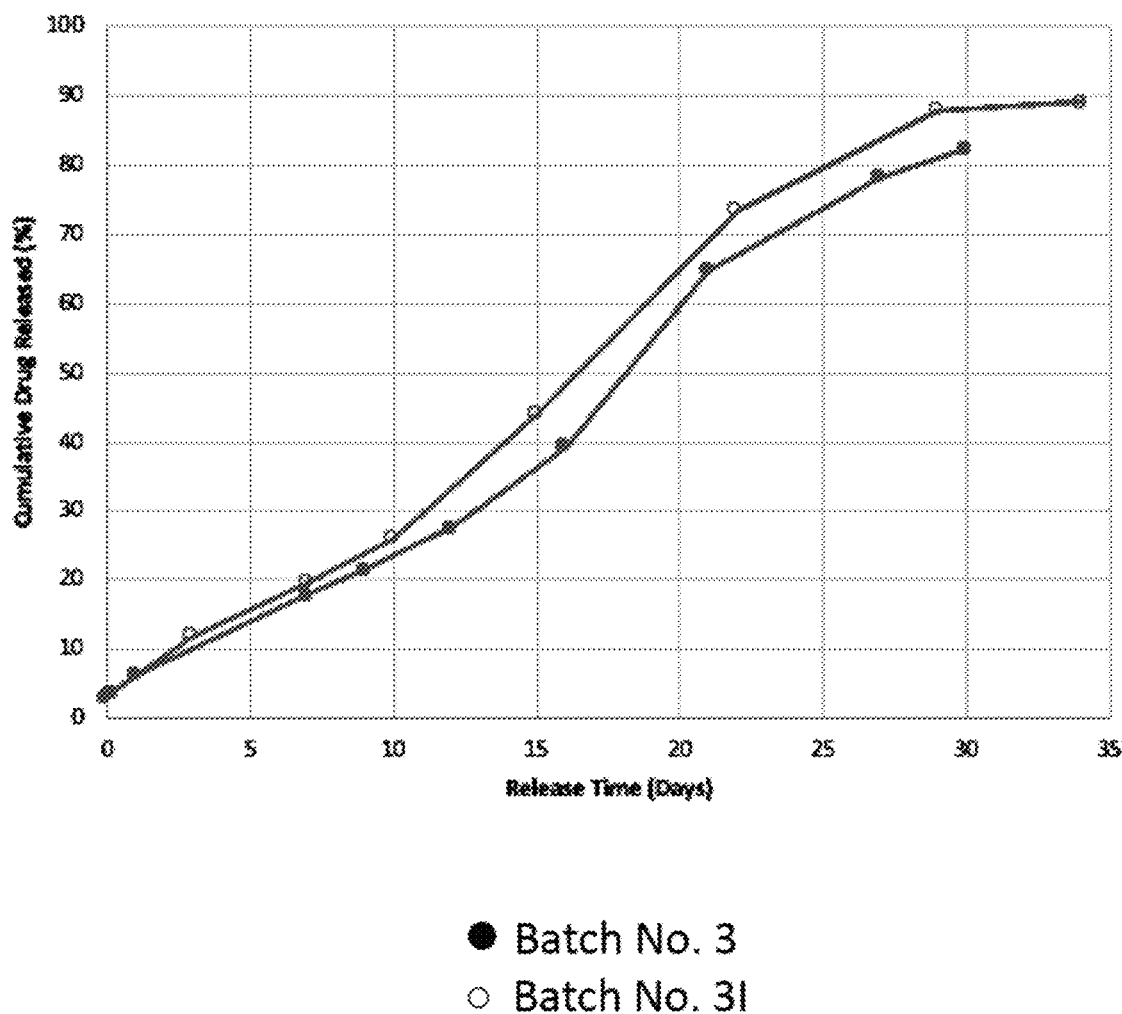
FIG. 4 is a graph showing in vitro cumulative lurasidone release over time from non-irradiated and irradiated lurasidone-encapsulating polymer microspheres.

FIG. 4 is a graph comparing in vitro cumulative lurasidone release over time from Batch Nos. 3 and 3I. FIG. 4 demonstrates that Batch Nos. 3 and 3I have a low initial burst release, and that the release profile of the microsphere formulation is not adversely impacted by sterilization of the polymer microspheres via irradiation.

Example 5

Preparation of Lurasidone-Encapsulated Polymer Microspheres—Batch Nos. 4 & 4I

Following the general procedure described in Example 1 and illustrated in FIG. 1, the DP was formed by dissolving 120 g of 7502A polymer (IV=0.20 dL/g) in 800 g of DCM and 400 g of BA (DCM/BA (2:1)), followed by addition of lurasidone (180 g) with mixing until completely dissolved. The DP was filtered and pumped at a flow rate of 25 mL/min into a Levitronix® BPS-i100 integrated pump system operating at 3,500 RPM. The CP comprising 0.35% PVA and 10 mM phosphate buffer (pH=7.6) was also pumped into the homogenizer at a flow rate of 2 L/min (CP:DP=80:1).

The formed or forming microspheres exited the homogenizer and entered the SRV. Deionized water was added to the SRV. Solvent removal was achieved using water washing and a hollow fiber filter. The bulk suspension was collected via filtration and lyophilized to obtain a free-flowing powder.

A portion of the powder was subjected to 25 kGy gamma irradiation under ambient temperature. The non-irradiated portion (Batch No. 4) had an average particle size of 15 μm ($D_{50}$), a drug load of 60.5 wt %, and a molecular weight of 16.9 kDa. The irradiated portion (Batch No. 4I) had an average particle size of 15 μm ($D_{50}$), a drug load of 60.0 wt %, and a molecular weight of 15.9 kDa.

Figure 5:
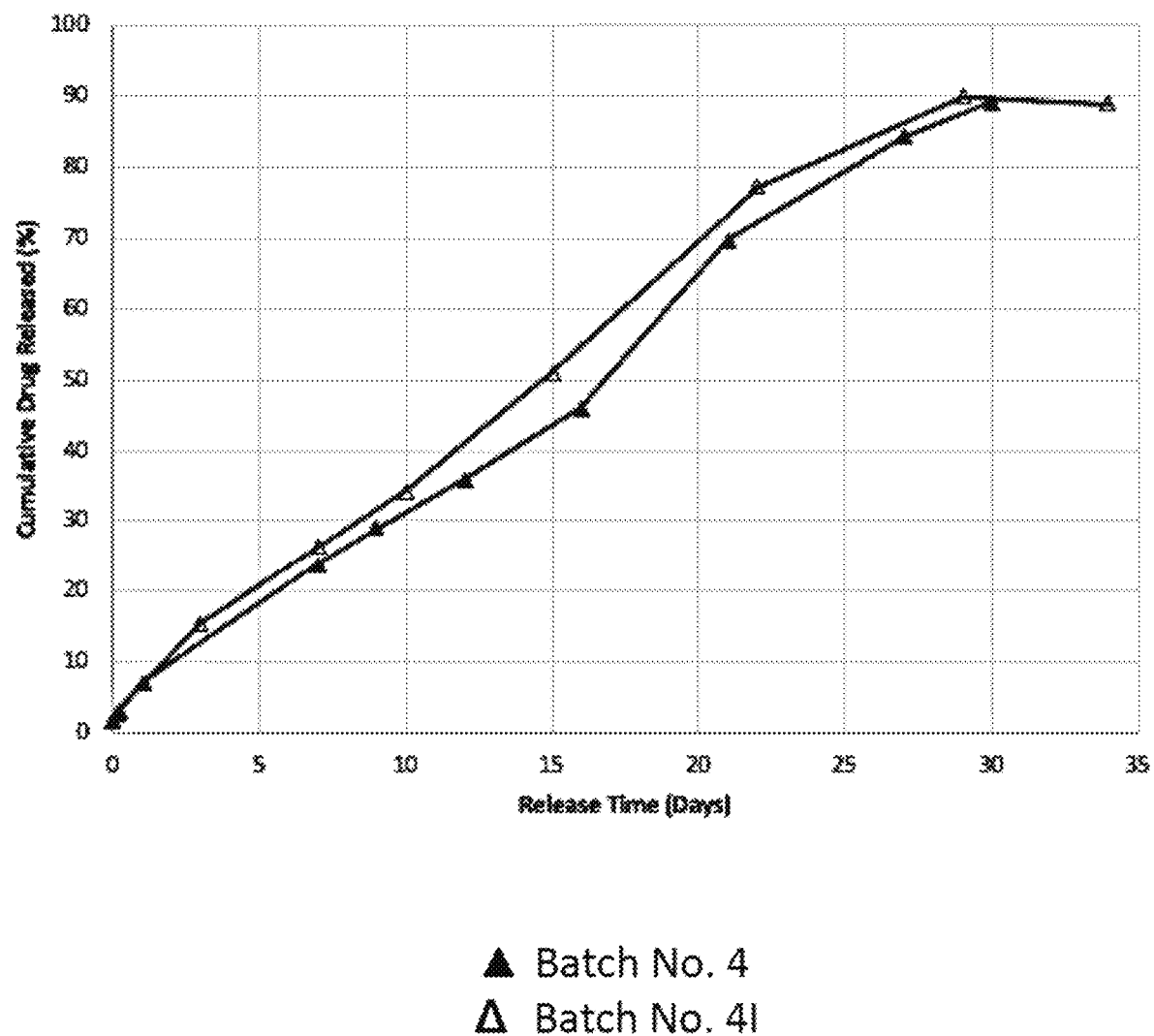
FIG. 5 is a graph showing in vitro cumulative lurasidone release over time from non-irradiated and irradiated lurasidone-encapsulating polymer microspheres.

FIG. 5 is a graph comparing in vitro cumulative lurasidone release over time from Batch Nos. 4 and 4I. FIG. 5 demonstrates that Batch Nos. 4 and 4I have a low initial burst release, and that the release profile of the microsphere formulation is not adversely impacted by sterilization of the polymer microspheres via irradiation.

Example 6

Preparation of Lurasidone-Encapsulated Polymer Microspheres — Batch Nos. 5 & 5I

Following the general procedure described in Example 1 and illustrated in FIG. 1, the DP was formed by dissolving 120 g of 7503A polymer (IV=0.29 dL/g) in 800 g of DCM and 400 g of BA (DCM/BA (2:1)), followed by addition of lurasidone (180 g) with mixing until completely dissolved. The DP was filtered and pumped at a flow rate of 25 mL/min into a Levitronix® BPS-i100 integrated pump system operating at 3,500 RPM. The CP comprising 0.35% PVA and 10 mM phosphate buffer (pH=7.6) was also pumped into the homogenizer at a flow rate of 2 L/min (CP:DP=80:1).

The formed or forming microspheres exited the homogenizer and entered the SRV. Deionized water was added to the SRV. Solvent removal was achieved using water washing and a hollow fiber filter. The bulk suspension was collected via filtration and lyophilized to obtain a free-flowing powder.

A portion of the powder was subjected to 25 kGy gamma irradiation under ambient temperature. The non-irradiated portion (Batch No. 5) had an average particle size of 18 μm ($D_{50}$), a drug load of 58.7 wt %, and a molecular weight of 29.9 kDa. The irradiated portion (Batch No. 5I) had an average particle size of 18 μm ($D_{50}$), a drug load of 58.8 wt %, and a molecular weight of 27.2 kDa.

Figure 6:
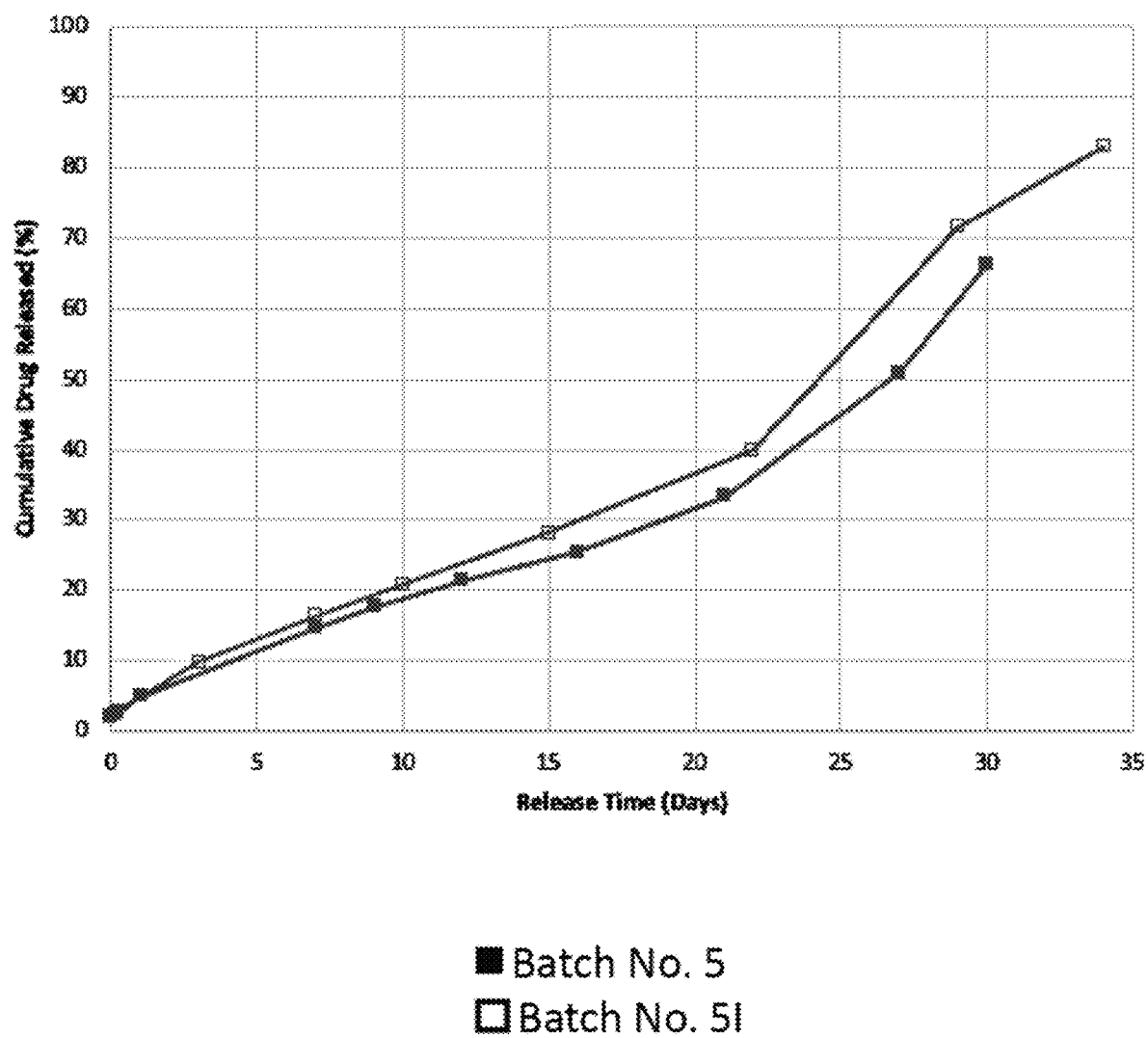
FIG. 6 is a graph showing in vitro cumulative lurasidone release over time from non-irradiated and irradiated lurasidone-encapsulating polymer microspheres.

FIG. 6 is a graph comparing in vitro cumulative lurasidone release over time from Batch Nos. 5 and 5I. FIG. 6 demonstrates that Batch Nos. 5 and 5I have a low initial burst release, and that the release profile of the microsphere formulation is not adversely impacted by sterilization of the polymer microspheres via irradiation.

Example 7

Preparation of Lurasidone-Encapsulated Polymer Microspheres—Batch Nos. 6 & 6I

Following the general procedure described in Example 1 and illustrated in FIG. 1, the DP was formed by dissolving 120 g of 752 H polymer (IV=0.21 dL/g) in 800 g of DCM and 400 g of BA (DCM/BA (2:1)), followed by addition of lurasidone (180 g) with mixing until completely dissolved. The DP was filtered and pumped at a flow rate of 25 mL/min into a Levitronix® BPS-i100 integrated pump system operating at 3,500 RPM. The CP comprising 0.35% PVA and 10 mM phosphate buffer (pH=7.6) was also pumped into the homogenizer at a flow rate of 2 L/min (CP:DP=80:1).

The formed or forming microspheres exited the homogenizer and entered the SRV. Deionized water was added to the SRV. Solvent removal was achieved using water washing and a hollow fiber filter. The bulk suspension was collected via filtration and lyophilized to obtain a free-flowing powder.

A portion of the powder was subjected to 25 kGy gamma irradiation under ambient temperature. The non-irradiated portion (Batch No. 6) had an average particle size of 16 μm ($D_{50}$), a drug load of 59.4 wt %, and a molecular weight of 15.6 kDa. The irradiated portion (Batch No. 6I) had an average particle size of 16 μm ($D_{50}$), a drug load of 60.1 wt %, and a molecular weight of 14.9 kDa.

Figure 7:
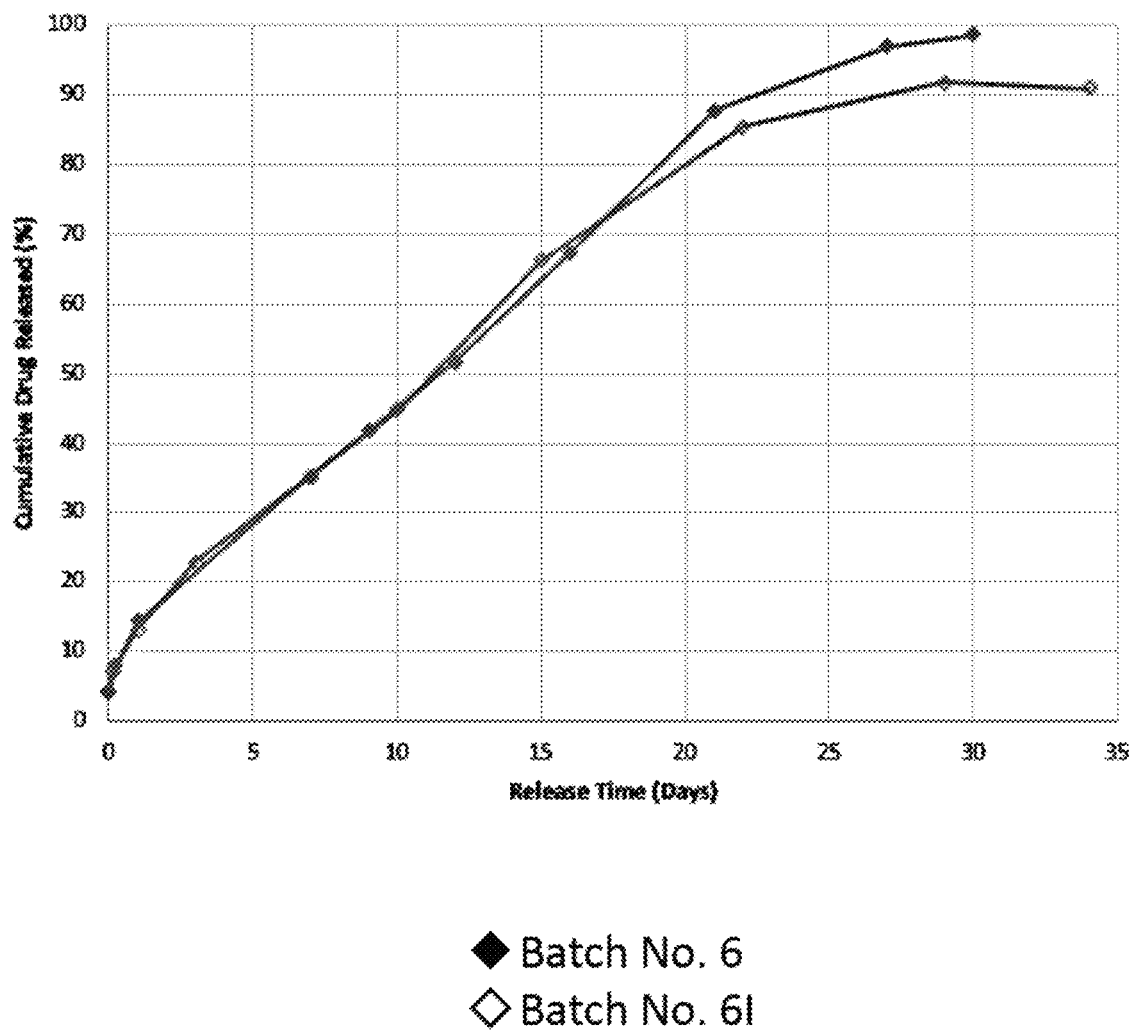
FIG. 7 is a graph showing in vitro cumulative lurasidone release over time from non-irradiated and irradiated lurasidone-encapsulating polymer microspheres.

FIG. 7 is a graph comparing in vitro cumulative lurasidone release over time from Batch Nos. 6 and 6I. FIG. 7 demonstrates that Batch Nos. 6 and 6I have a low initial burst release, and that the release profile of the microsphere formulation is not adversely impacted by sterilization of the polymer microspheres via irradiation.

Figure 8:
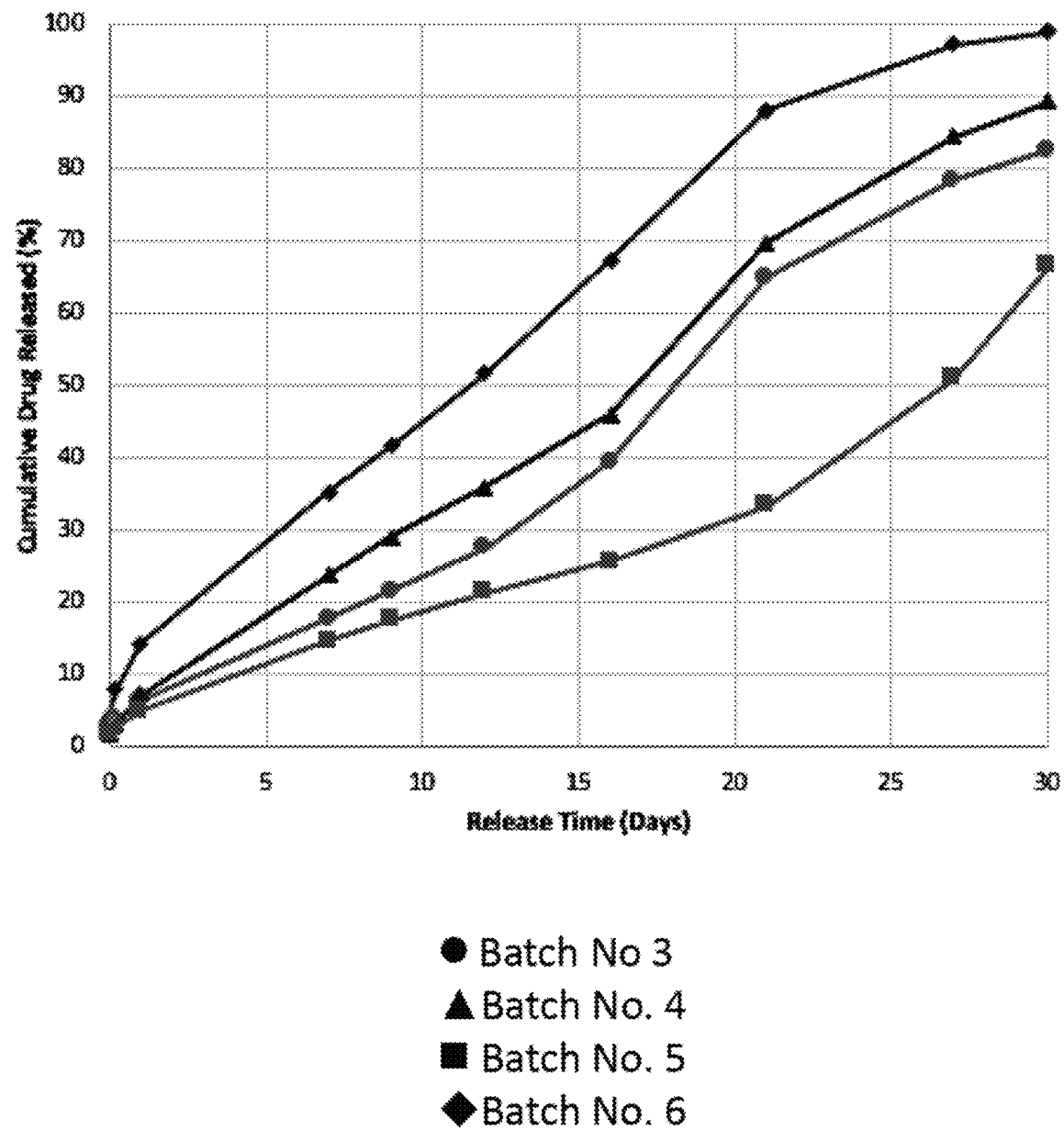
FIG. 8 is a graph showing in vitro cumulative lurasidone release over time from non-irradiated lurasidone-encapsulating polymer microspheres.
Figure 9:
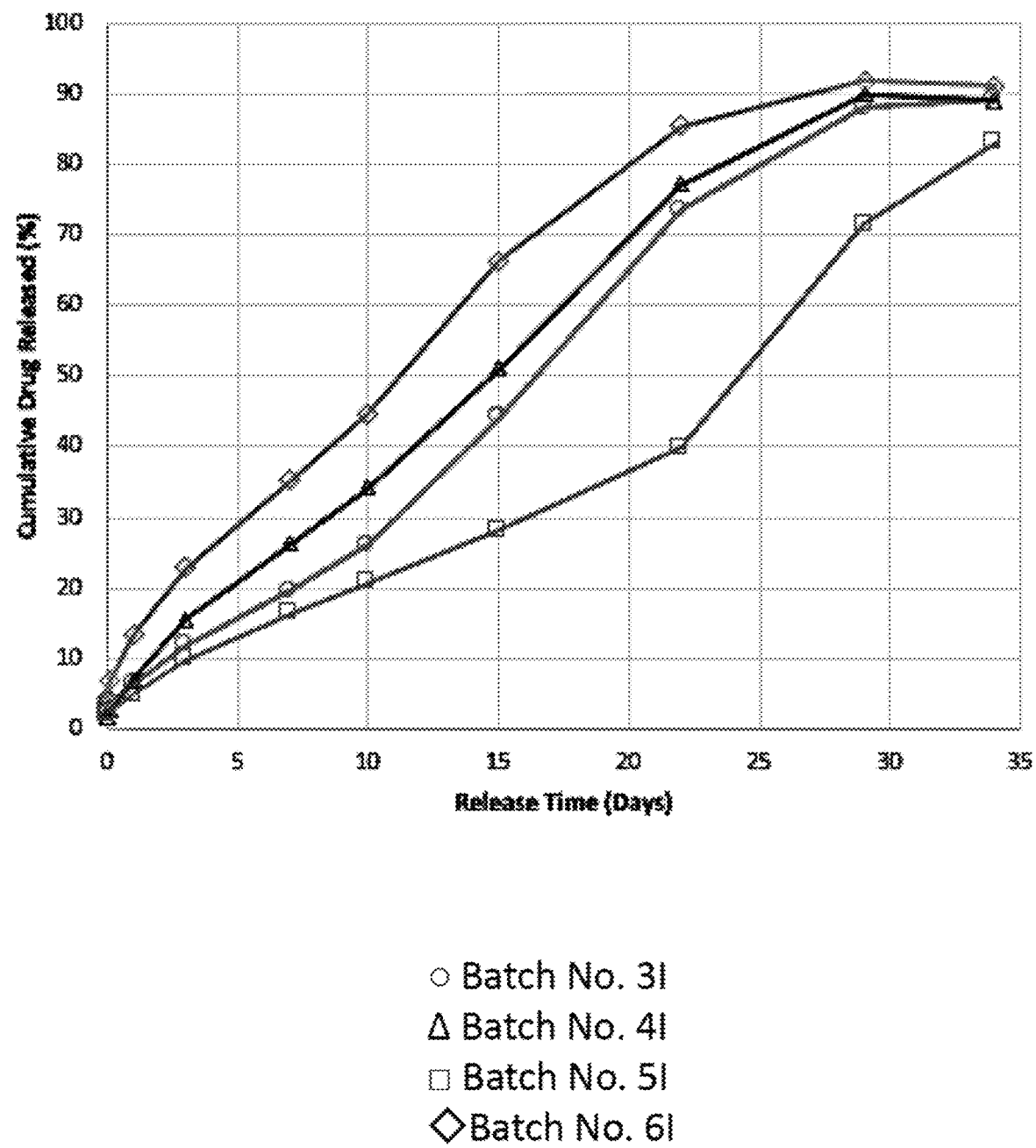
FIG. 9 is a graph showing in vitro cumulative lurasidone release over time from irradiated lurasidone-encapsulating polymer microspheres.

FIG. 8 is a graph comparing in vitro cumulative lurasidone release over time from Batch Nos. 3, 4, 5, and 6. FIG. 9 is a graph comparing in vitro cumulative lurasidone release over time from Batch Nos. 3I, 4I, 5I, and 6I.

Example 8

Pharmacokinetics Study in Dogs of Batch Nos. 3, 3I, 4, 4I, 5, 5I, 6, and 6I

Figure 10:
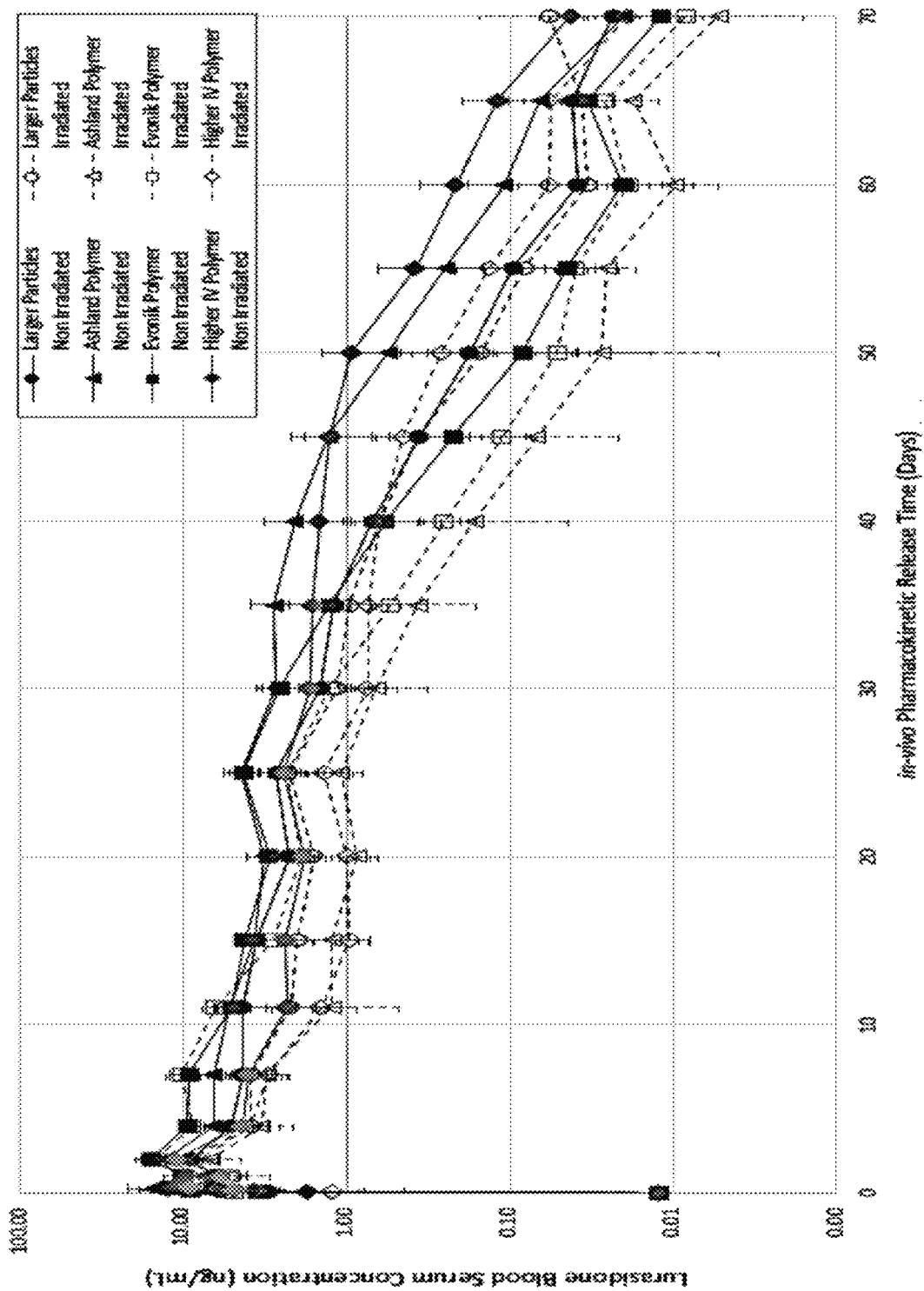
FIG. 10 is a graph showing results of a pharmacokinetics study in dogs using non-irradiated and irradiated lurasidone-encapsulating polymer microspheres.

The pharmacokinetic profile of lurasidone following a subcutaneously injected dose of time-released lurasidone formulation in dogs was studied. The dogs received a 10 mg/kg dose of the indicated Batch No., having a lurasidone concentration of 100 mg/mL. Blood samples were collected at 1, 3, 6, 24, 48, 96, 168, 264, 360, 480, 600, 720, 840, 960, 1080, 1200, 1320, 1440, 1560, and 1680 hour timepoints. FIG. 10 is a graph showing the measured mean blood concentration (ng/mL) of lurasidone as a function of time for Batches Nos. 3, 3I, 4, 4I, 5, 5I, 6, and 6I.

Example 9

Preparation of Lurasidone-Encapsulated Polymer Microspheres—Batch No. 7

Following the general procedure described in Example 1 and illustrated in FIG. 1, the DP was formed by dissolving 15 g of 7502 A polymer (IV=0.19 dL/g) in 133.3 g of DCM and 66.70 g of BA (DCM/BA (2:1)), followed by addition of lurasidone (35 g) with mixing until completely dissolved. The DP was filtered and pumped at a flow rate of 25 mL/min into a Levitronix® BPS-i100 integrated pump system operating at 3,500 RPM. The CP comprising 0.35% PVA (but with no buffer) was also pumped into the homogenizer at a flow rate of 2 L/min (CP:DP=80:1).

The formed or forming microspheres exited the homogenizer and entered the SRV. Deionized water was added to the SRV. Solvent removal was achieved using water washing and a hollow fiber filter. The bulk suspension was collected via filtration and lyophilized to obtain a free-flowing powder.

Figure 11:
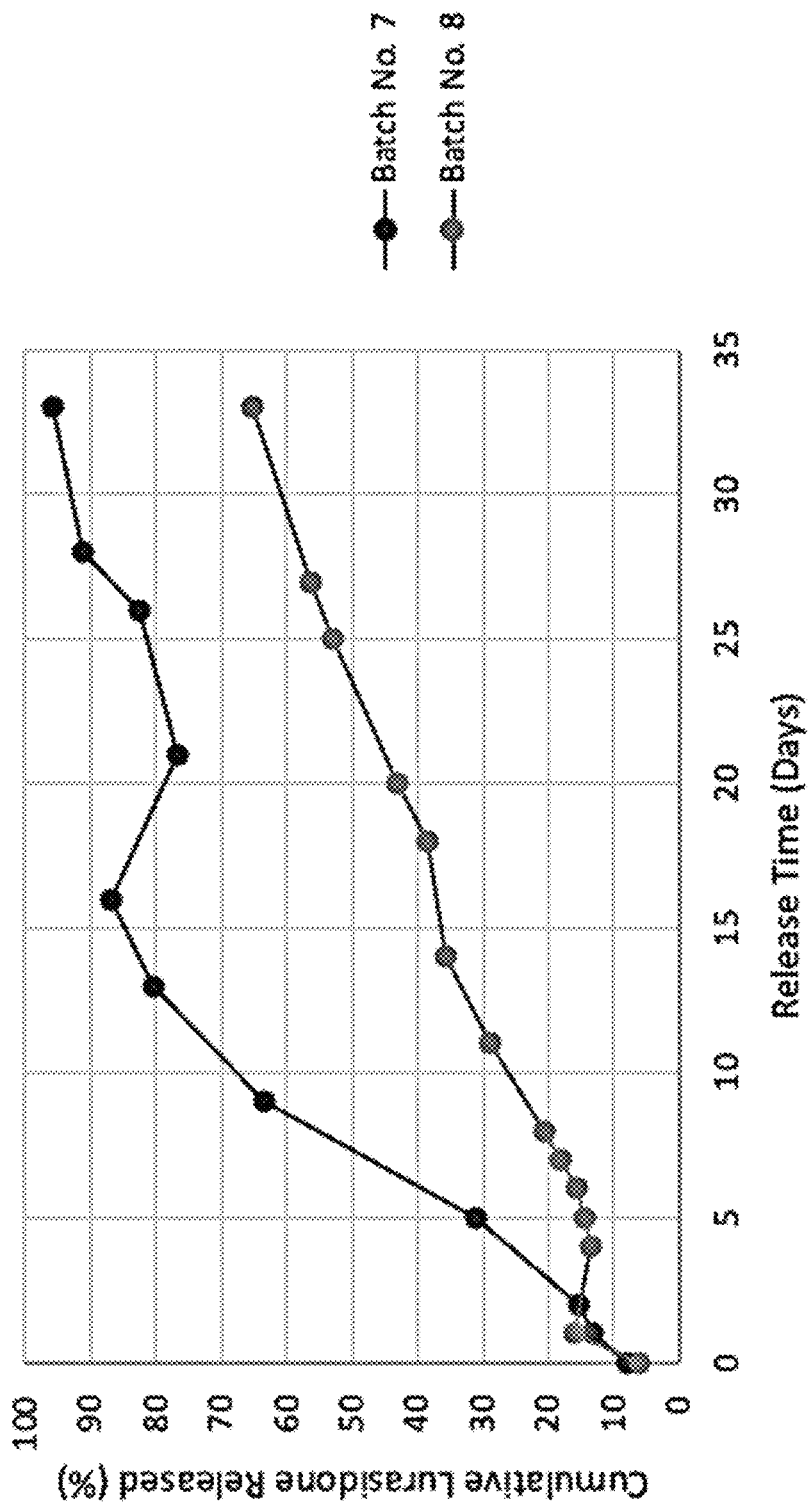
FIG. 11 is a graph showing in vitro cumulative lurasidone release over time from lurasidone-encapsulating polymer microspheres.

Batch No. 7 had an average particle size of 16 μm ($D_{50}$), a drug load of 63% (encapsulation efficiency=91% based on a target drug load of 70%), and a molecular weight of 16.6 kDa. FIG. 11 is a graph showing in vitro cumulative lurasidone release over time from Batch No. 7.

Example 10

Preparation of Lurasidone-Encapsulated Polymer Microspheres—Batch No. 8

Following the general procedure described in Example 1 and illustrated in FIG. 1, the DP was formed by dissolving 3.0 g of 7507 A polymer (IV=0.56 dL/g) in 26.67 g of DCM and 13.33 g of BA (DCM/BA (2:1)), followed by addition of lurasidone (7.0 g) with mixing until completely dissolved. The DP was filtered and pumped at a flow rate of 25 mL/min into a Levitronix® BPS-i100 integrated pump system operating at 3,500 RPM. The CP comprising 0.35% PVA (but with no buffer) was also pumped into the homogenizer at a flow rate of 2 L/min (CP:DP=80:1).

The formed or forming microspheres exited the homogenizer and entered the SRV. Deionized water was added to the SRV. Solvent removal was achieved using water washing and a hollow fiber filter. The bulk suspension was collected via filtration and lyophilized to obtain a free-flowing powder.

Batch No. 8 had an average particle size of 18 μm ($D_{50}$), a drug load of 59% (encapsulation efficiency=84% based on a target drug load of 70%), and a molecular weight of 62.0 kDa. FIG. 11 is a graph showing in vitro cumulative lurasidone release over time from Batch No. 8.

In use, the microspheres may be suspended in a diluent for administration (injection). The diluent may generally contain a thickening agent, a tonicity agent, and a surfactant. The thickening agent may include carboxymethyl cellulose-sodium (CMC-Na) or other suitable compounds. An appropriate viscosity grade and suitable concentration of CMC-Na may be selected so that the viscosity of the diluent is 3 cps or higher. Generally, a viscosity of about 10 cps is suitable; however, a higher viscosity diluent may be preferred for larger microspheres to minimize the settling of microspheres in the suspension.

Uniform microsphere suspension without particle settling will result in a consistent delivered dose during drug administration by injection. To have a tonicity of the diluent closer to the biological system, about 290 milliosmole (mOsm), solutes such as mannitol, sodium chloride, or any other acceptable salt may be used. The diluent may also contain a buffer salt to maintain the pH of the composition. Typically, the pH is maintained around a physiologically relevant pH by adjusting the buffer content as needed (pH about 7 to about 8).

The aspects disclosed herein are not intended to be exhaustive or to be limiting. A skilled artisan would acknowledge that other aspects or modifications to instant aspects can be made without departing from the spirit or scope of the invention. The aspects of the present disclosure, as generally described herein and illustrated in the figures, can be arranged, substituted, combined, separated, and designed in a wide variety of different configurations, all of which are contemplated herein.

Unless otherwise specified, "a," "an," "the," "one or more of," and "at least one" are used interchangeably. The singular forms "a", "an," and "the" are inclusive of their plural forms. The recitations of numerical ranges by endpoints include all numbers subsumed within that range (e.g., 1 to 5 includes 1, 1.5, 2, 2.75, 3, 3.80, 4, 5, etc.). The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

When reference is made to the term "each," it is not meant to mean "each and every, without exception." For example, if reference is made to microsphere formulation comprising polymer microspheres, and "each polymer microsphere" is said to have a particular API content, if there are 10 polymer microspheres, and two or more of the polymer microspheres have the particular API content, then that subset of two or more polymer microspheres is intended to meet the limitation.

The term "about" in conjunction with a number is simply shorthand and is intended to include ±10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about," the exact number is intended. In other words, "10" means 10.

What is claimed is:

1. A microsphere formulation, comprising:
   polymer microspheres, each polymer microsphere comprising:
   an active pharmaceutical ingredient consisting of lurasidone or a pharmaceutically acceptable salt thereof; and
   a biodegradable polymer wherein the biodegradable polymer comprises an acid terminated poly(D,L-lactide-co-glycolide) with lactide:glycolide ratio of about 75 to about 25, and wherein the biodegradable polymer has an inherent viscosity of about 0.14 dL/g to about 0.56 dL/g,
   wherein each polymer microsphere comprises a drug load of lurasidone of greater than or equal to 55% by weight of the polymer microsphere, and
   wherein the polymer microspheres have a particle size of less than or equal to 25 μm ($D_{50}$).

2. The microsphere formulation of claim 1, wherein the pharmaceutically acceptable salt of lurasidone is lurasidone HCl.

3. The microsphere formulation of claim 1, wherein each polymer microsphere has a lurasidone drug load of from 55% to about 70% by weight of the polymer microsphere; and wherein the polymer microspheres have a particle size of from about 9 μm to 25 μm ($D_{50}$).

4. The microsphere formulation of claim 3, wherein the polymer microspheres have been irradiated.

5. A pharmaceutical composition comprising the microsphere formulation of claim 1.

6. The microsphere formulation of claim 1, characterized in that about 75% to 100% of the lurasidone is released over a period of about 30 days of injection into a subject, but not more than about 20% of the lurasidone has been released within about 24 hours of injection into the subject.

7. The microsphere formulation of claim 3, wherein the polymer microspheres have a particle size of between about 14 μm ($D_{50}$) and 25 μm ($D_{50}$).

8. The microsphere formulation of claim 3, wherein:
   the biodegradable polymer comprises an acid terminated poly(D,L-lactide-co-glycolide) with lactide:glycolide of about 75: about 25, and wherein the biodegradable polymer has an inherent viscosity of from about 0.14 dL/g to about 0.21 dL/g.

9. The microsphere formulation of claim 3, wherein:
   the biodegradable polymer comprises an acid terminated poly(D,L-lactide-co-glycolide) with lactide:glycolide of about 75: about 25, and wherein the biodegradable polymer has an inherent viscosity of from about 0.14 dL/g to about 0.29 dL/g.

10. The microsphere formulation of claim 3, wherein the polymer microspheres have a particle size of from about 14 μm ($D_{50}$) to about 20 μm ($D_{50}$).

11. A pharmaceutical composition comprising the microsphere formulation of claim 3.

12. The microsphere formulation of claim 3, characterized in that about 75% to 100% of the lurasidone is released over a period of about 30 days of injection into a subject, but not more than about 20% of the lurasidone has been released within about 24 hours of injection into the subject.

13. A microsphere formulation, comprising:
   polymer microspheres, each polymer microsphere comprising:
   an active pharmaceutical ingredient consisting of lurasidone HCl; and
   a biodegradable polymer comprising an acid terminated poly(D,L-lactide-co-glycolide) ("PLGA") with lactide:glycolide of about 75: about 25 and an inherent viscosity of from about 0.14 dL/g to about 0.56 dL/g,
   wherein each polymer microsphere has a lurasidone drug load of from 55% to about 70% by weight of the polymer microsphere;
   wherein the polymer microspheres have a particle size of about 14 μm ($D_{50}$) to about 25 μm ($D_{50}$); and
   wherein the microsphere formulation is characterized in that about 75% to 100% of the lurasidone is released over a period of about 30 days of injection into a subject, but not more than about 20% of the lurasidone has been released within about 24 hours of injection into the subject.

14. A pharmaceutical composition comprising the microsphere formulation of claim 13.

15. The microsphere formulation of claim 13, wherein the inherent viscosity of the PLGA is from about 0.14 dL/g to about 0.29 dL/g.

16. The microsphere formulation of claim 13, wherein the inherent viscosity of the PLGA is from about 0.14 dL/g to about 0.21 dL/g.

\* \* \* \* \*